US011826955B2

(12) United States Patent
Sun et al.

(10) Patent No.: US 11,826,955 B2
(45) Date of Patent: Nov. 28, 2023

(54) MAGNETICALLY-DRIVABLE MICROROBOT

(71) Applicant: City University of Hong Kong, Kowloon (HK)

(72) Inventors: Dong Sun, Kowloon (HK); Tanyong Wei, Kowloon (HK); Lidai Wang, Kowloon (HK); Dongfang Li, Kowloon (HK); Yachao Zhang, Kowloon (HK); Shuxun Chen, Kowloon (HK)

(73) Assignee: City University of Hong Kong, Kowloon (HK)

( * ) Notice: Subject to any disclaimer, the term of this patent is extended or adjusted under 35 U.S.C. 154(b) by 208 days.

(21) Appl. No.: 17/128,345

(22) Filed: Dec. 21, 2020

(65) Prior Publication Data
US 2022/0024121 A1 Jan. 27, 2022

Related U.S. Application Data

(60) Provisional application No. 63/055,963, filed on Jul. 24, 2020.

(51) Int. Cl.
*B29C 64/153* (2017.01)
*A61B 5/00* (2006.01)
(Continued)

(52) U.S. Cl.
CPC .......... *B29C 64/153* (2017.08); *A61B 5/0095* (2013.01); *A61B 34/30* (2016.02); *B33Y 70/10* (2020.01); *B33Y 80/00* (2014.12); *C08K 5/053* (2013.01); *C08K 5/103* (2013.01); *H01F 1/0054* (2013.01); *H02K 1/02* (2013.01);
(Continued)

(58) Field of Classification Search
CPC ....... B29C 64/153; B33Y 80/00; B33Y 70/10; A61B 34/30; A61B 5/0095; B82Y 25/00; C08K 5/053; C08K 5/103; C08K 2201/01; C08K 2201/011; C08K 2201/018
See application file for complete search history.

(56) References Cited

U.S. PATENT DOCUMENTS 9,326,823 B2 5/2016 McMillian et al.
9,782,342 B2 10/2017 Asmatulu et al.
(Continued)

FOREIGN PATENT DOCUMENTS

KR 10-1737440 3/2017

OTHER PUBLICATIONS

Small_2019_Liao_Magnetically Driven Undulatory Microswimmers Integrating Multiple Rigid Segments (Year: 2019).*
(Continued)

*Primary Examiner* — Yunju Kim
(74) *Attorney, Agent, or Firm* — RENNER KENNER GREIVE BOBAK TAYLOR & WEBER

(57) ABSTRACT

A method of making a magnetically-drivable microrobot that is suitable for carrying and delivering cells includes photo-curing a photo-curable material composition to form a body of the magnetically-drivable microrobot. The photo-curable material composition includes a degradable component, a structural component, a magnetic component, and a photo-curing facilitation composition including a photoinitiator component and a photosensitizer component.

18 Claims, 18 Drawing Sheets
(4 of 18 Drawing Sheet(s) Filed in Color)

(51) Int. Cl.
| | |
|---|---|
| *A61B 34/30* | (2016.01) |
| *B33Y 70/10* | (2020.01) |
| *B33Y 80/00* | (2015.01) |
| *C08K 5/053* | (2006.01) |
| *C08K 5/103* | (2006.01) |
| *H01F 1/00* | (2006.01) |
| *H02K 1/02* | (2006.01) |
| *B82Y 25/00* | (2011.01) |
| *B82Y 30/00* | (2011.01) |
| *B82Y 35/00* | (2011.01) |

(52) U.S. Cl.
CPC .............. *B82Y 25/00* (2013.01); *B82Y 30/00* (2013.01); *B82Y 35/00* (2013.01); *C08K 2201/01* (2013.01); *C08K 2201/011* (2013.01); *C08K 2201/018* (2013.01)

(56) References Cited

U.S. PATENT DOCUMENTS

| | | |
|---|---|---|
| 2012/0165957 A1 | 6/2012 | Everland et al. |
| 2013/0045160 A1 | 2/2013 | Ham et al. |
| 2013/0338498 A1 | 12/2013 | Emelianov et al. |
| 2014/0378796 A1 | 12/2014 | Chen et al. |
| 2018/0153633 A1* | 6/2018 | Rodriguez-Navarro ..................... A61B 34/73 |
| 2019/0001025 A1 | 1/2019 | Ferrari et al. |
| 2019/0076371 A1 | 3/2019 | Sum et al. |

OTHER PUBLICATIONS

Degradable Magnetic Composites for Minimally Invasive Interventions: Device Fabrication, Targeted Drug Delivery, and Cytotoxicity Tests. Advanced Material. 2016, 28(3): 533-538.

A microrobotic system guided by photoacoustic computed tomography for targeted navigation in intestines in vivo. Science Robotics, 2019, 4(32): eaax0613.

Development of a magnetic microrobot for carrying and delivering targeted cells. Science Robotics, 2018, 3(19):eaat8829.

* cited by examiner

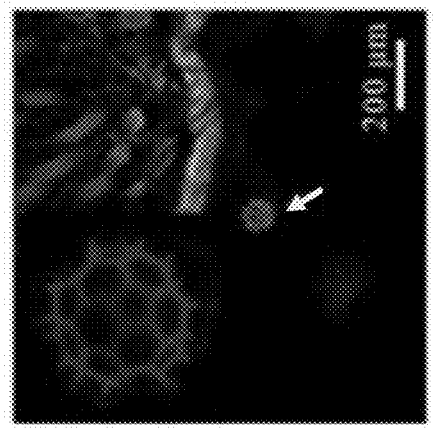
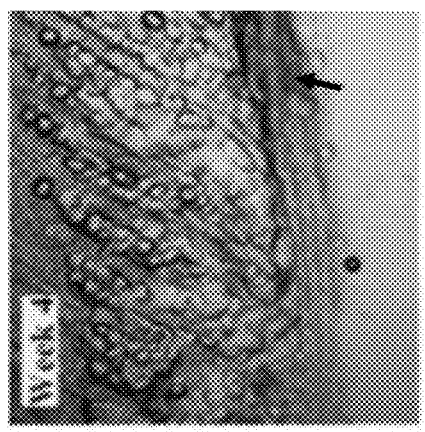
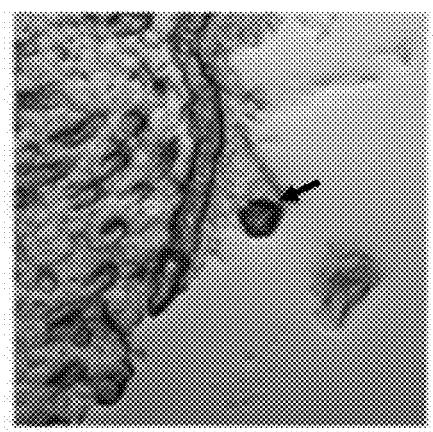
Figure 13A
Figure 13B
Figure 13C
Figure 13D

MAGNETICALLY-DRIVABLE MICROROBOT

TECHNICAL FIELD

The invention relates to magnetically-drivable microrobots and a method of making magnetically-drivable microrobots.

BACKGROUND

Microrobots are commonly used for biomedical applications in in vivo and in vitro environments as they are small and can be controlled relatively easily. Some existing biomedical microrobots are non-degradable while other biomedical microrobots are degradable. Non-degradable microrobots are relatively difficult to be removed from the environment in which they are placed and hence are not particularly suited for in vivo applications. On the other hand, degradable microrobots may have relatively weak structures, making them not suitable for carrying cells or the like.

SUMMARY

In a first aspect, there is provided a method of making a magnetically-drivable microrobot. The microrobot is arranged for carrying and delivering cells, drugs, medicament, or the like. The method comprises photo-curing a photo-curable material composition to form a body of the magnetically-drivable microrobot. The photo-curable material composition comprises a degradable component, a structural component, a magnetic component, and a photo-curing facilitation composition comprising a photoinitiator component and a photosensitizer component. The degradable component may be used as a material matrix. The structural component may be used to provide strength or structural integrity to the body. The magnetic component makes the body magnetically-drivable. The photoinitiator component and the photosensitizer component may be used to crosslink various components of the photo-curable material composition.

The photo-curable material composition may include one or more additional components. Alternatively, the photo-curable material composition consists essentially of the degradable component, the structural component, the magnetic component, and the photo-curing facilitation composition with the photoinitiator component and the photosensitizer component.

The degradable component may comprise poly(ethylene glycol) diacrylate (PEGDA) or like poly(ethylene glycol) (PEG) derivatives. In one example, the degradable component includes 74 vol % or about 74 vol % PEDGA (with respect to the photo-curable material composition).

The structural component may comprise pentaerythritol triacrylate (PETA). The structural component may comprise at least 20 vol %, at least 24 vol %, or at least 25% vol % PETA (with respect to the photo-curable material composition).

Optionally, a ratio of vol % of PEGDA to vol % of PETA is between about 2:1 to about 4:1, about 3:1, or 3:1.

The magnetic component may comprise $Fe_3O_4$ particles. The $Fe_3O_4$ particles may include $Fe_3O_4$ nanoparticles. The $Fe_3O_4$ particles may be of no more than 2 vol % (with respect to the photo-curable material composition).

The photoinitiator component may comprise parbenate. The photosensitizer component may comprise 2-isopropyl-9H-thioxanthen-9-one.

In one embodiment, the photo-curable material composition consists essentially of: PEGDA, PETA, $Fe_3O_4$ nanoparticles, photoinitiator, and photosensitizer. In one example, the photo-curable material composition includes about 74 vol % PEGDA, about 24 vol % PETA, about 2 vol % $Fe_3O_4$ nanoparticles, and traces of the photoinitiator and the photosensitizer.

Optionally, the photo-curing (e.g., laser writing) is performed selectively using lithography techniques such as 3D laser lithography or multiphoton lithography.

Optionally, the method further comprises coating or applying a contrast agent on at least part of the body. The contrast agent may include a material that makes the microrobot more readily imagable by an imaging device.

Optionally, the method further comprises coating or otherwise applying a photoacoustic imaging contrast agent on at least part of the body. The photoacoustic imaging contrast agent may include gold. In the embodiment in which the photoacoustic imaging contrast agent forms a coating, the coating may include one or more layers. In one example, the coating may have a thickness in an order of nanometers, e.g., 10 nm.

Optionally, the method further comprises forming the photo-curable material composition by mixing the degradable component and the structural component based on a first ratio to form a first mixture, and mixing the first mixture with the magnetic component based on a second ratio to form a second mixture. The method may further comprise determining or optimizing a composition of the photo-curable material composition, in particular the first and second ratios, prior to the forming of the photo-curable material composition. The determination or optimization, hence the first and second ratios, depends on the required properties or applications of the microrobots.

Optionally, the method further comprises mixing the photo-curable material composition prior to the photo-curing. The mixing may be performed using a mixer or shaker machine.

Optionally, the method further comprises developing the formed body after the photo-curing. The developing may include drying the body, cooling the body, blowing air over the body, etc.

The body formed may comprise a porous body with a three-dimensional structure having burr members. The three-dimensional structure may be of any shape, e.g., generally spherical.

Optionally, the photo-curing of the photo-curable material composition forms respective bodies of a plurality of magnetically-drivable microrobots. The bodies may be formed sequentially (one after another) or substantially simultaneously. Adjacent bodies may be overlapped, e.g., mechanically engaged, with or without direct material connection. In one example, the mechanical engagement without direct material connect may include two or more interconnected eyelets or rings.

Optionally, the method further comprises attaching or loading cells, drugs, medicament, or the like, to the body and/or the coating.

In a second aspect, there is provided one or more magnetically-drivable microrobots made using, at least, the method of the first aspect. The one or more microrobots are suited for biomedical applications.

In a third aspect, there is provided a method of manipulating a magnetically-drivable microrobot, such as the magnetically-drivable microrobot of the second aspect. The method comprises imaging, using photoacoustic imaging apparatus, the magnetically-drivable microrobot in an environment; and, based on the imaging, applying a magnetic field to the magnetically-drivable microrobot to move the magnetically-drivable microrobot in the environment. The environment may be an in vivo environment such as a blood vessel. The photoacoustic imaging apparatus may include a probe, an optical fiber, etc.

Optionally, the imaging is performed in real time, e.g., dynamically or continuously, as the magnetically-drivable microrobot is moved by the magnetic field so as to image the moving magnetically-drivable microrobot and hence to track it. The magnetic field may be a gradient magnetic field.

In a fourth aspect, there is provided a system for manipulating a magnetically-drivable microrobot, such as the magnetically-drivable microrobot of the second aspect. The system comprises a photoacoustic imaging apparatus arranged to image the magnetically-drivable microrobot in an environment, and a magnetic field generator, formed by one or more coils, arranged to provide a magnetic field to move the magnetically-drivable microrobot in the environment. The environment may be an in vivo environment such as a blood vessel. The photoacoustic imaging apparatus may include a probe, an optical fiber, etc.

Optionally, the system further comprises a controller operably connected with the magnetic field generator to control operation of the magnetic field generator based on feedback from the photoacoustic imaging apparatus and/or a user input. The magnetic field generator may be a gradient magnetic field generator.

Optionally, the photoacoustic image apparatus is arranged to image the magnetically-drivable microrobot in real time, e.g., dynamically or continuously, as the magnetically-drivable microrobot is moved by the magnetic field so as to image the moving magnetically-drivable microrobot and hence to track it.

Other features and aspects of the invention will become apparent by consideration of the detailed description and accompanying drawings. Any feature(s) described herein in relation to one aspect or embodiment may be combined with any other feature(s) described herein in relation to any other aspect or embodiment as appropriate and applicable.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Embodiments of the invention will now be described, by way of example, with reference to the accompanying drawings, in which:

FIG. 13A is a confocal scan image showing a histological section of tissue implanted with a microrobot made with 75 vol % PEGDA and 25 vol % PETA at week 4;

FIG. 13B is fluorescence image of the histological section of tissue implanted with the microrobot of FIG. 13A;

FIG. 13C is a confocal scan image showing a histological section of tissue implanted with a microrobot made with too vol % PETA at week 4;

FIG. 13D is fluorescence image of the histological section of tissue implanted with the microrobot of FIG. 13C;

FIG. 19A is a photoacoustic image of an in vivo navigation of a cell-loaded microrobot conducted in the inferior vena cava of a nude mice at position a;

DETAILED DESCRIPTION

Figure 1:
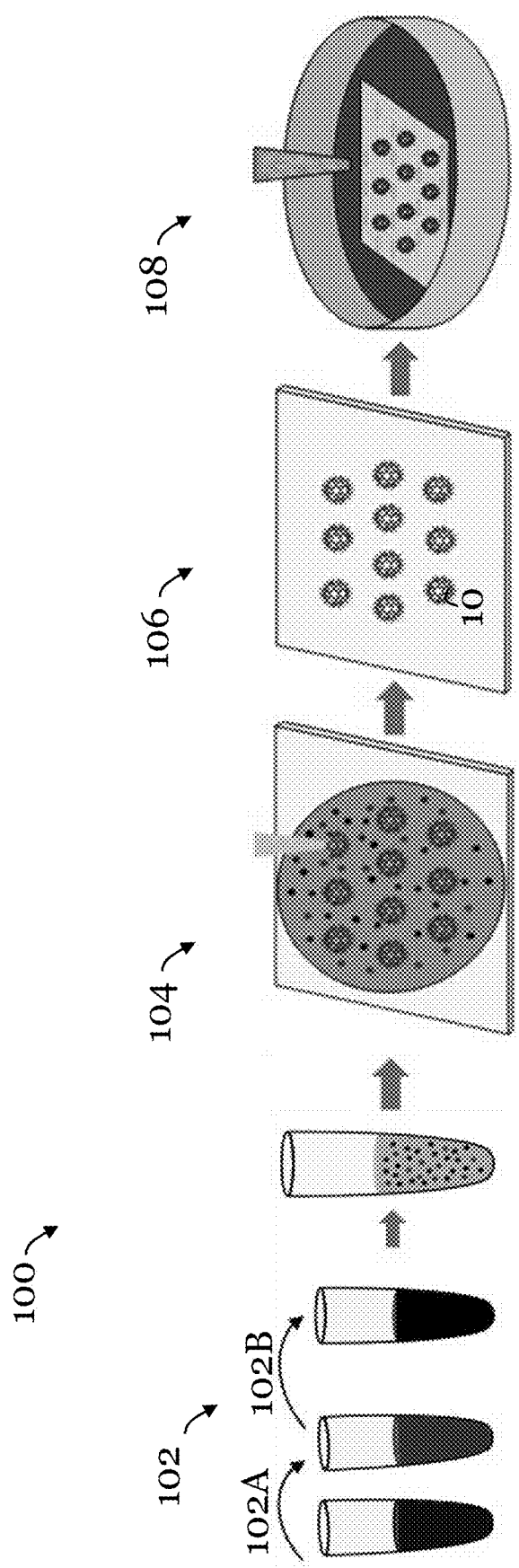
FIG. 1 is a schematic diagram illustrating a method of making a magnetically-drivable microrobot in one embodiment of the invention.

FIG. 1 shows a method 100 of making magnetically-drivable microrobots 10 for carrying and delivering cells in one embodiment of the invention. The microrobots may be loaded with cells or the like. In one exemplary application, the microrobots may be guided inside vascular tissues using real-time photoacoustic (PA) imaging and ultrasound (US) imaging technologies, during routing of the tissues, allowing detection of optical adsorption with high resolutions.

The microrobots 10 are fabricated using optimized photo-curable composite materials including a degradable component arranged to provide degradability of the microrobot, a mechanical or structural component arranged to provide mechanical strength or support of the microrobot, and a magnetic component arranged to provide magnetic actuation capability (that allows the microrobot to respond to magnetic manipulation). The composition of the microrobot materials can be optimized based on applications, in view of, among other factors, degradability, mechanical strength (for carrying cells, drugs, or the like), and magnetic actuation capability. The composition further includes a photo-curing facilitation composition including a photoinitiator and a photosensitizer that are used to crosslink the components in the composition. The degradable component may include a derivative of polyethylene glycol (PEG), such as poly(ethylene glycol) diacrylate (PEGDA), which is used in drug delivery and tissue engineering-based applications. The structural component may include a derivative of acrylate, such as pentaerythritol triacrylate (PETA). The magnetic component may include magnetic or ferromagnetic particles such as $Fe_3O_4$ particles, in particular $Fe_3O_4$ nanoparticles. The photoinitiator and photosensitizer may include parbenate and 2-isopropyl-9H-thioxanthen-9-one, respectively.

The method 100 of making the microrobots begins in step 102. In 102A of step 102, the degradable component, which is used as a material matrix, is first combined with the structural component in a first ratio to form a first mixture, and to provide mechanical strength to the microrobots. Then, in 102B of step 102, the magnetic component is mixed with the first mixture of the degradable component and the structural component in a second ratio to obtain a second mixture, to provide a material composition with magnetic actuation capability. The mixing in 102A and 102B of step 102 may be performed using a mixer or shaker. The composition of the photo-curable material composition, in particular the first and second ratios, may be determined or optimized before step 102, to achieve optimized degradability and mechanical strength depending on the required application. Specifically, the first ratio can be determined based on the structural integrity of burdening cell tensile forces. The second ratio can be determined based on the actuation capability requirements and fabrication constrains.

After step 102, in step 104, the optimized material composition is photo-cured using lithography, such as 3D laser lithography or multiphoton lithography, to define multiple microrobots. In the illustrated embodiment, multiple microrobots 10 are defined as separate microrobots without material connection.

Subsequently, in step 106, the photo-cured composition is developed to form multiple microrobots 10 for loading cells or the like. In the illustrated embodiment, the formed microrobots 10 include a porous body with a three-dimensional structure that is generally spherical and having multiple burr members. The burr members extend substantially orthogonally from an outer surface of the porous body.

In one embodiment, the method 100 may include coating or applying a contrast agent, e.g. gold, on at least part of the body formed. The contrast agent may be a photoacoustic imaging contrast agent that facilitates photoacoustic imaging or photoacoustic imaging based tracking of the body. The coating may have a thickness in the order of nanometers, e.g., 10 nm.

After step 106, in step 108, cells are loaded onto the microrobots 10 so that the cell-loaded microrobots can be applied to an environment to carry and/or deliver cells. The cells are loaded or attached to the body or to the coating of the photoacoustic imaging contrast agent. The cells may be loaded or attached between adjacent burr members of the same microrobot or different burr members of adjacent microrobots.

Figure 2:
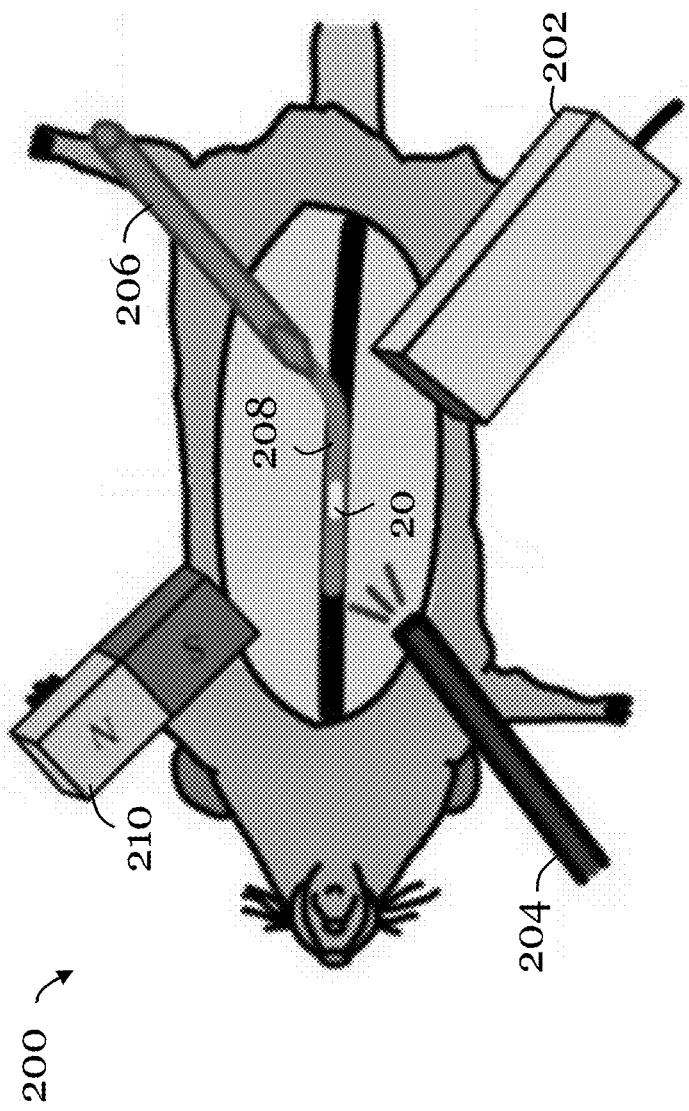
FIG. 2 is a schematic diagram illustrating a system for manipulating a magnetically-drivable microrobot made using the method of FIG. 1 in one embodiment of the invention.

FIG. 2 shows a system 200 for manipulating magnetically-drivable microrobots 20 loaded with cells in a live mice. The magnetically-drivable microrobots 20 may be the ones made based on the method 100 in one embodiment of the invention. In this embodiment, a clusters of cell-loaded microrobots are delivered into the blood vessel of the mice. The microrobots 20 are engineered with optically absorbing materials to ensure a high optical absorption coefficient and high contrast to hemoglobin molecules in the visible spectrum.

The system 200 includes a photoacoustic imaging apparatus having a probe 202 and an optical fiber 204 arranged to image the microrobots 20 in the blood vessel (e.g., inferior vena cava) of the mice. The system 200 also includes a sharp needle 206 and a catheter 208 covered with the needle 206 for piercing and delivering the cell-loaded microrobots 20 into the blood vessel. The system 200 further includes a magnetic field generator 210, formed by one or more coils in this embodiment, arranged to provide a magnetic field to interact with and hence move the microrobot 20 in the mice. The magnetic field generator 210 may be a gradient magnetic field generator. The photoacoustic image apparatus may be arranged to image the microrobot 20 in real time, e.g., dynamically or continuously, as the microrobot 20 is moved or otherwise manipulated by the magnetic field. As such, the movement of the magnetically-drivable microrobot 20 can be tracked by imaging. The system 200 may further comprise a controller (not shown) operably connected with the magnetic field generator 210 to control operation of the magnetic field generator 210 based on feedback from the photoacoustic imaging apparatus and/or a user input.

Fabrication of Magnetically-Drivable Microrobots

In one experimentation, a photo-curable material composition including PEGDA (Sigma, 437441), PETA (Sigma, 246794), magnetic nanoparticle solution (100 nm size, 260 mg/mL suspended in gamma-butyrolactone (GBL), customized by chemicell GmbH), photoinitiator (Parbenate, Easepi EDB, Curease Chemical, China), and photosensitizer (2-Isopropyl-9H-thioxanthen-9-one, Easepi ITX, Curease Chemical, China) was used to make the microrobots. Before forming the microrobots using lithography, the prepolymer solution (photo-curable material composition) were mixed using a vortex shaker. The composite was then drop-casted on a clean glass substrate and loaded in Nanoscribe, a commercial two-photon direct writing system (GmbH, Germany) for structures written with a 63× oil immersion objective (numerical aperture of 1.4 from Zeiss). The substrate was then developed in toluene (Sigma, 179965) and isopropanol alcohol (IPA, Sigma, 67-63-0), and dried in fume hood via airflow.

Cells were then loaded onto the formed microrobots. The formed microrobots were sterilized using UV irradiation and treated in a plasma cleaner for 30 s. Human iPSC-MSC-GPx3 was trypsinized and re-suspended at a concentration of $10^5$ cells/mL. This cell solution was then drop-casted on the microrobots and incubated for 15 mins in a humidified incubator at 37° C. with 5% $CO_2$ for cell attachment. Then the additional 2 ml culture medium was added. After overnight cultivation, the cells stably attached to the microrobots. The microrobots were dehydrated in a critical point dryer (LEICA EM CPD300), and the morphology of microrobot with cells were observed under SEM (FE-SEM, FEI Nova 450), as discussed in further detail below.

In addition, a cluster of microrobots was prepared for photoacoustic tomography (PAT) experiments. In this example, the microrobots were manufactured one after the other. In order to avoid the spread of microrobots, the manufactured microrobots had small overlap (e.g., mechanical engagement, with or without direct connection) with adjacent microrobots by the burr members, and the array of connected microrobots formed a square. In this example, a cluster of ten microrobots was established in four production lines: the first three production lines contained three microrobots, and the last production line contained only one microrobot.

Optimization of Photo-Curable Material Composition

To determine or optimize the photo-curable material composition (in particular the first and second ratios described with respect to the method 100 of FIG. 1) for specific applications, degradability and mechanical strength requirements of the microrobots are considered.

FIGS. 3 to 5F show the degradation and mechanical test results of the microrobots made from different ratios of PEGDA (vol %) and PETA (vol %). The tested ratios include 90:10, 75:25, 50:50, 25:75, and 0:100. During fabrication of the microrobots under test, the different ratios of materials were doped with same amount of Rhodamine B-PEG-Thiol (RB-PEG-SH).

For the degradation test, the fabricated microrobots were immersed in a PBS environment. At different time instants, the microrobot image was captured (Zeiss Fluorescence Microscope) and the fluorescence intensity of the microrobot was analyzed with the ImageJ software. From FIG. 3, it can be seen that the fluorescence intensity of microrobot with a high PEGDA ratio decays more rapidly, indicating the microrobot with high PEGDA ratio benefits its degradability.

Figure 4:
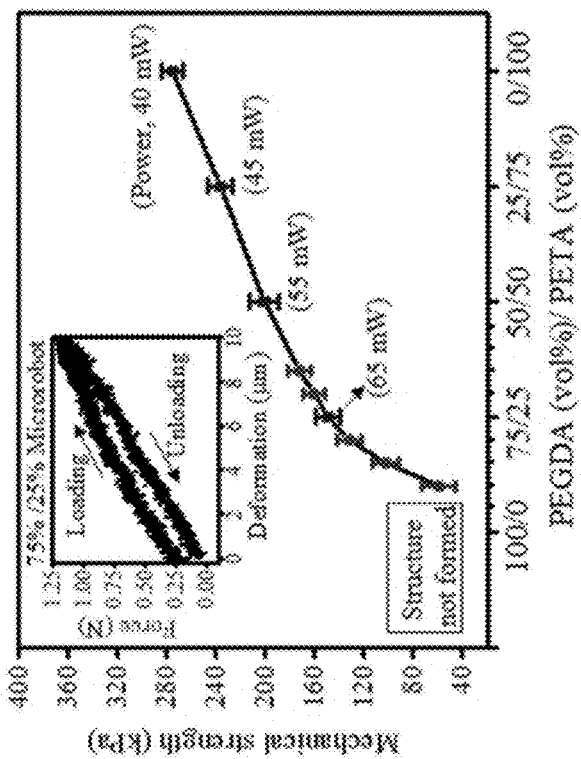
FIG. 4 is a graph showing the mechanical test results of the microrobots made from different ratios of PEGDA (vol %) to PETA (vol %)
Figure 3:
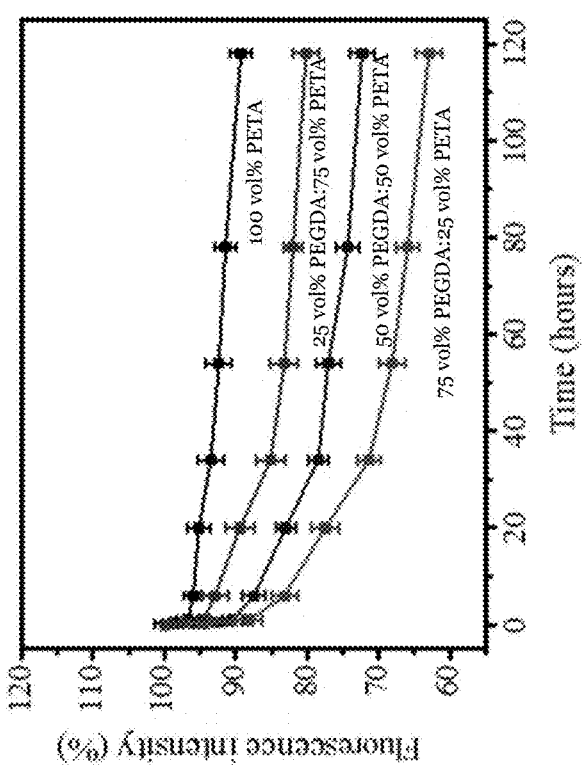
FIG. 3 is a graph showing the degradation test results of the microrobots made from different ratios of PEGDA (vol %) to PETA (vol %)
Figure 5C:
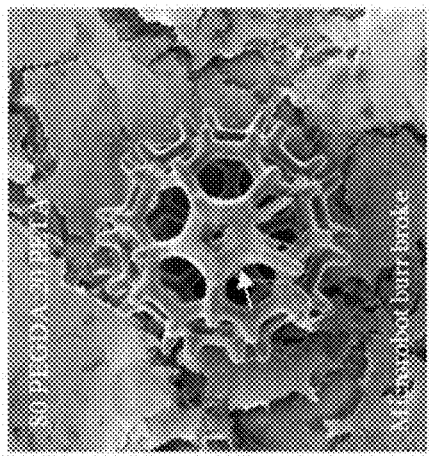
FIG. 5C is a scanning electron microscopic image of a microrobot made using 80 vol % PEGDA: 20 vol % PETA, showing that the burr is broken.
Figure 5F:
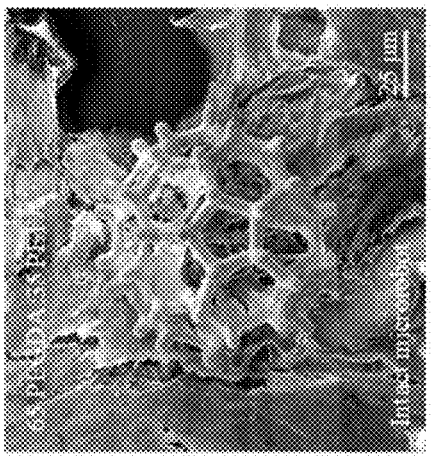
FIG. 5F is a scanning electron microscopic image of a microrobot made using 65 vol % PEGDA: 35 vol % PETA, showing that the microrobot is intact.
Figure 5B:
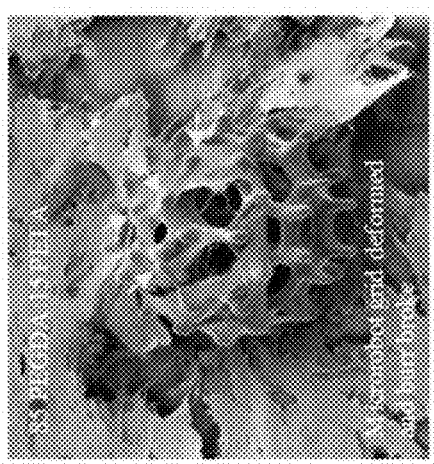
FIG. 5B is a scanning electron microscopic image of a microrobot made using 85 vol % PEGDA: 15 vol % PETA, showing that the microrobot grid is deformed and the burr is broken.
Figure 5E:
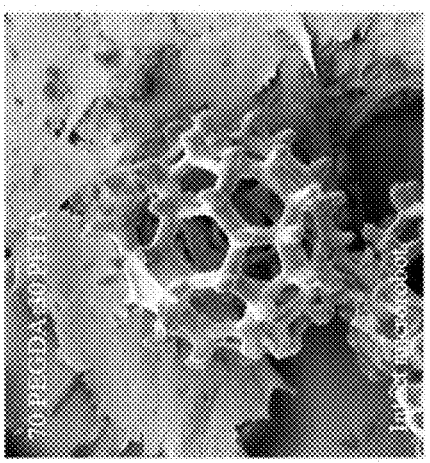
FIG. 5E is a scanning electron microscopic image of a microrobot made using 70 vol % PEGDA: 30 vol % PETA, showing that the microrobot is intact.
Figure 5A:
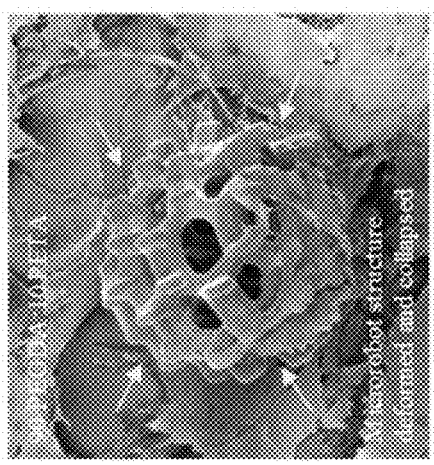
FIG. 5A is a scanning electron microscopic image of a microrobot made using 90 vol % PEGDA: 10 vol % PETA, showing that the microrobot structure is deformed and collapsed.
Figure 5D:
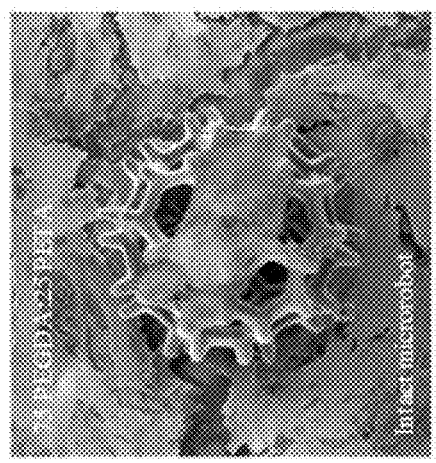
FIG. 5D is a scanning electron microscopic image of a microrobot made using 75 vol % PEGDA: 25 vol % PETA, showing that the microrobot is intact.

For the mechanical test, the fabricated microrobots were tested in a Hysitron TI950 Dual-Head Nano Indentation System. The mechanical strengths of microrobots as determined are shown in FIG. 4, in which the inset shows the mechanical test of microrobot in 75 vol % PEGDA:25 vol % PETA. As seen from FIG. 4, the mechanical strength of the microrobot increases as the ratio of PETA increases, and the material with a higher PETA composition requires less laser power in microrobot fabrication. These indicate that a higher PETA composition could benefit the structural integrity of the microrobots.

To determine the minimal PETA composition required for microrobot fabrication, the materials with different ratio of PEGDA and PETA were tested based on the structural integrity. It was found that a minimal composition of 10 vol % PETA was required to form a properly structured microrobot.

The microrobots with different ratios of PEGDA and PETA were then further evaluated based on the mechanical strength for carrying mesenchymal stem cells (MSCs). FIGS. 5A to 5F indicate that the microrobot with PETA lower than 25 vol % may collapse relatively easily after loading cells, and the microrobots with 25 vol % PETA or above may remain stable and intact when cells are loaded. In this example, it may be advantageous to use 75 vol % PEGDA and 25 vol % PETA in the composition of microrobot material, in order to provide optimal degradability and structural integrity.

Figure 6:
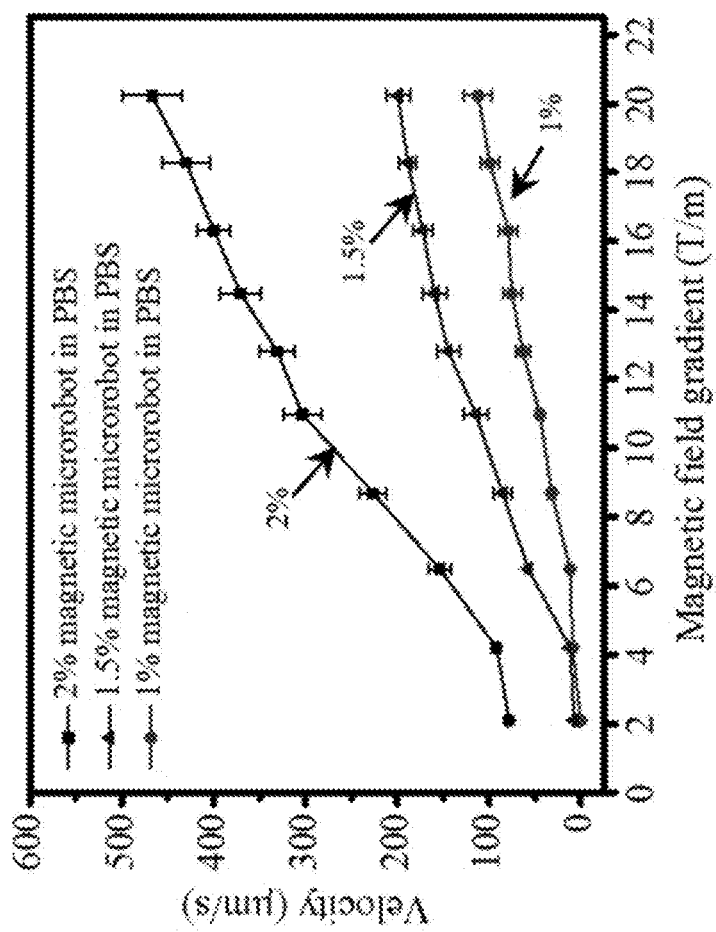
FIG. 6 is a graph showing the magnetic actuation capability of the microrobots made with different percentage of $Fe_3O_4$ nanoparticles.
Figure 7A:
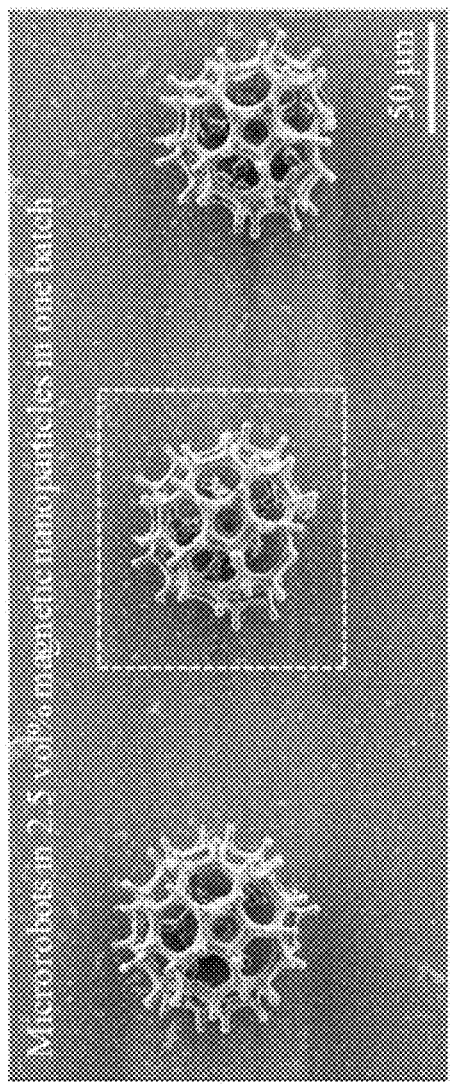
FIG. 7A is a scanning electron microscopic image of microrobots made using 2.5 vol % $Fe_3O_4$ nanoparticles.
Figure 7C:
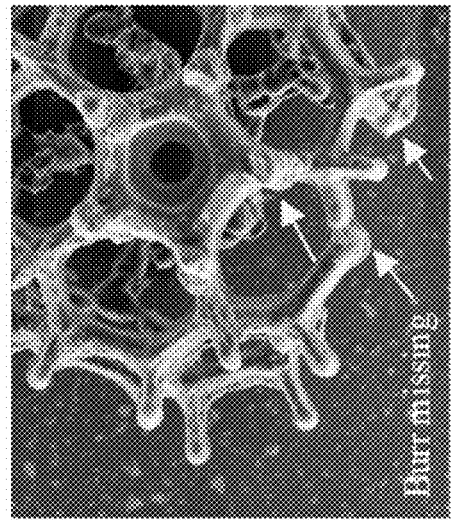
FIG. 7C is an enlarged scanning electron microscopic image of a section of the microrobot in FIG. 7B in the dotted-line rectangle, showing that the burr is missing.

FIGS. 6 to 7C illustrate the determination of the second ratio described with respect to the method 100 of FIG. 1, based on the magnetic actuation capability and fabrication constraint. Microrobots fabricated with 75:25 ratio of PEGDA (vol %) to PETA (col %), plus Fe3O4 nanoparticles at different ratios of 1 vol %, 1.5 vol %, and 2 vol %, were tested. It is shown that the microrobots could achieve an increased actuation speed as the ratio of the nanoparticles increases from 1 vol % to 2 vol %. In this example, the ratio of the magnetic component is limited to within 2 vol % as a higher ratio in the composition may reduce or block laser penetration, potentially making the microrobots defective.

Figure 7B:
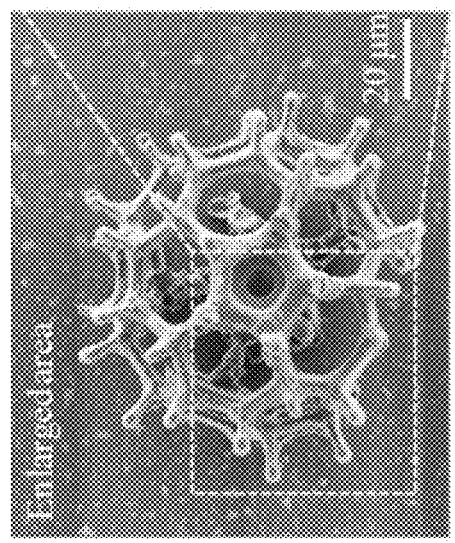
FIG. 7B is an enlarged scanning electron microscopic image of the microrobot in the dotted-line rectangle in FIG. 7A.

FIGS. 7A to 7C show the microrobots fabricated with a 2.5 vol % magnetic content. As the excessive magnetic component in the composite blocked laser writing during photo-curing, defects were found in the scanning electron microscopy (SEM) images. Therefore, in one example, 2 vol % magnetic nanoparticles were doped with the microrobot material of 75 vol % PEGDA and 25 vol % PETA for microrobot magnetic actuation. In this example, the composition of 74 vol % PEGDA, 24 vol % PETA and 2 vol % Fe3O4 nanoparticles solution was used in view of the above experimental results.

Degradability and Biocompatibility of Magnetically-Driven Microrobots

Figure 9:
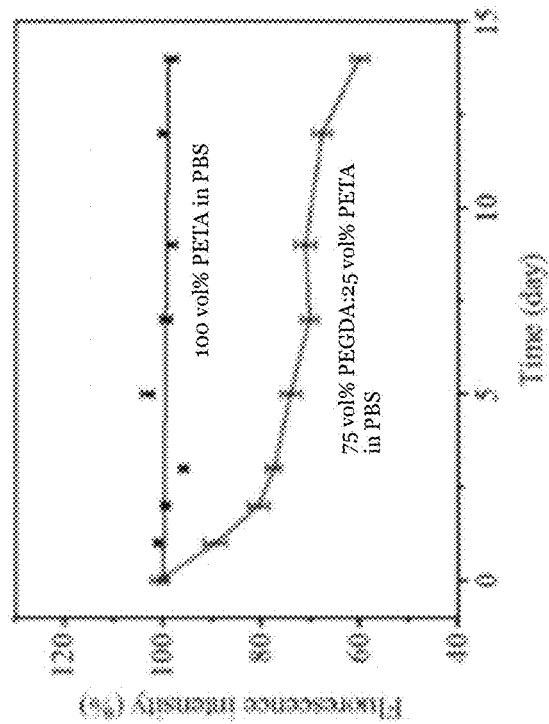
FIG. 9 is a graph showing the fluorescence signal of the microrobots made using different ratios of PEGDA to PETA in PBS.
Figure 8:
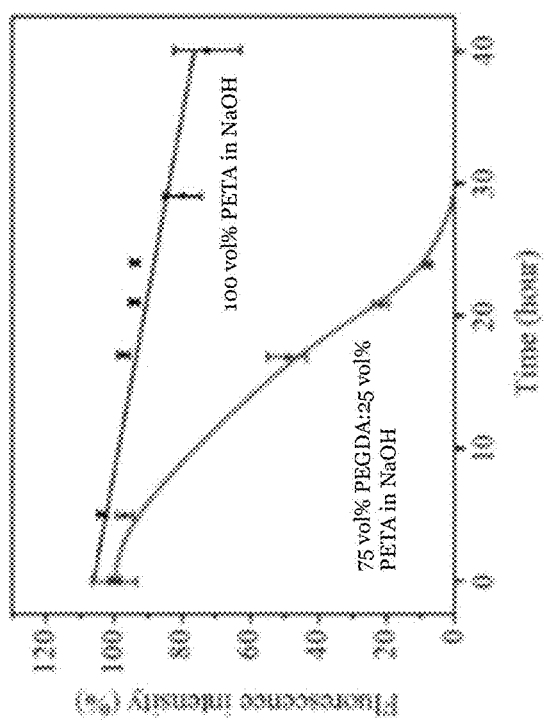
FIG. 8 is a graph showing the fluorescence signal of the microrobots made using different ratios of PEGDA to PETA in NaOH.
Figure 10A:
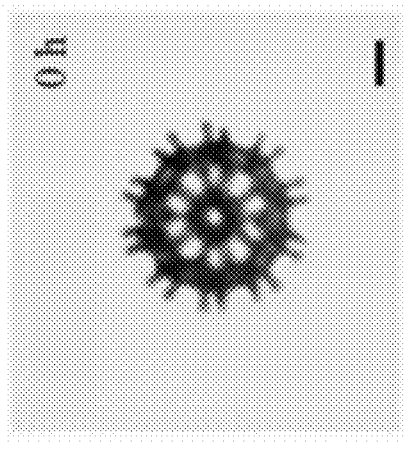
FIG. 10A is an image of the microrobot in NaOH initially.
Figure 10B:
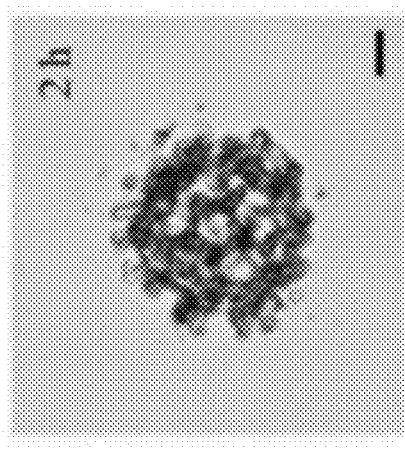
FIG. 10B is an image of the microrobot of FIG. 10A after 2 hours.
Figure 10C:
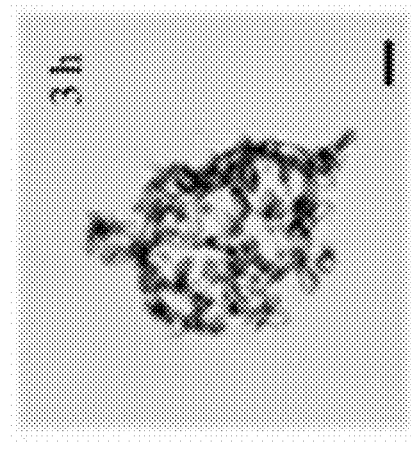
FIG. 10C is an image of the microrobot of FIG. 10A after 3 hours.
Figure 10D:
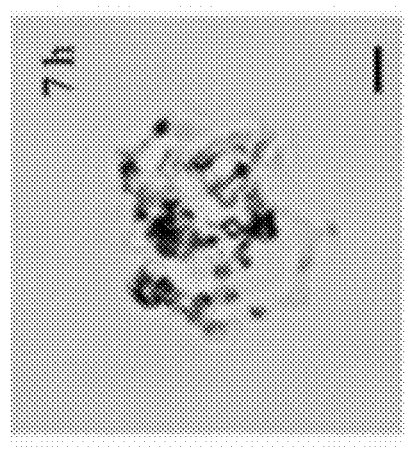
FIG. 10D is an image of the microrobot of FIG. 10A after 7 hours.

The degradability and biocompatibility of the designed microrobots were evaluated. FIGS. 8 and 9 illustrate the fluorescence signal of microrobots made of degradable 75 vol % PEGDA:25 vol % PETA hydrogel and hard-to-degrade 100 vol % PETA hydrogel in the NaOH solution and PBS environment, respectively. The result shows that the fluorescence intensity of the degradable 75 vol % PEGDA: 25 vol % PETA microrobots decreased by 92% within 24 hours in the NaOH solution, while that of hard-to-degrade 100 vol % PETA microrobots decreases by only 13% (FIG. 8). In the PBS environment, the fluorescence intensity of the degradable microrobots decreased by 40% after two-week incubation, while that of hard-to-degrade microrobots remained almost unchanged (FIG. 9). These results demonstrate that the fabricated microrobots can be degraded by hydrolysis, and degradation in alkaline environments is much faster than degradation in PBS.

Figure 11B:
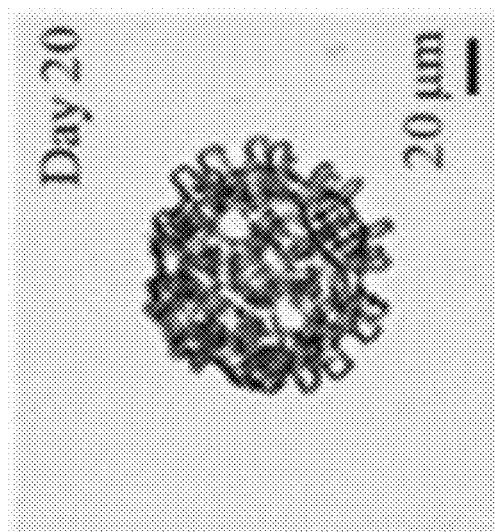
FIG. 11B is an image of the microrobot of FIG. 11A after 20 days.
Figure 11A:
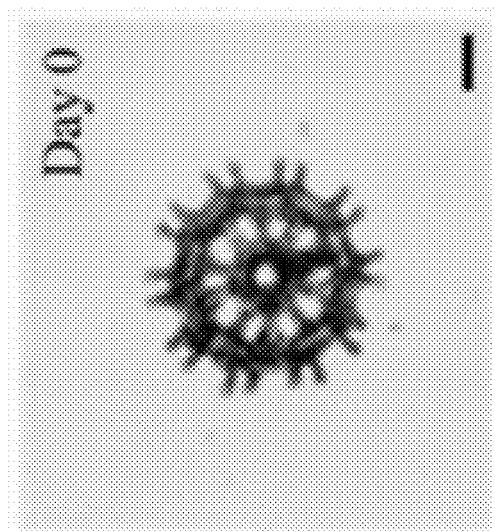
FIG. 11A is an image of the microrobot in PBS initially.
Figure 12B:
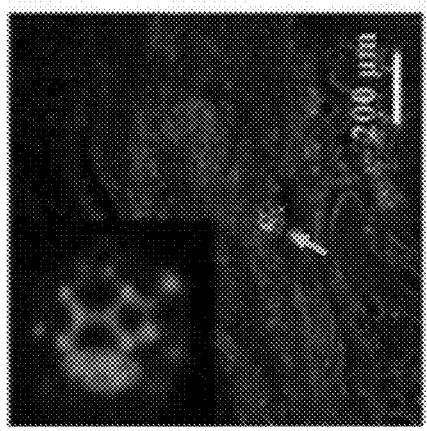
FIG. 12B is fluorescence image of the histological section of tissue implanted with the microrobot of FIG. 12A.
Figure 12D:
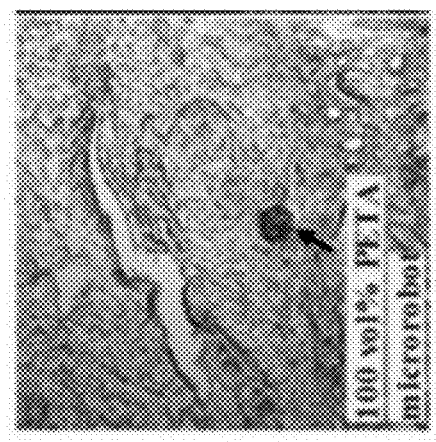
FIG. 12D is fluorescence image of the histological section of tissue implanted with the microrobot of FIG. 12C.
Figure 12A:
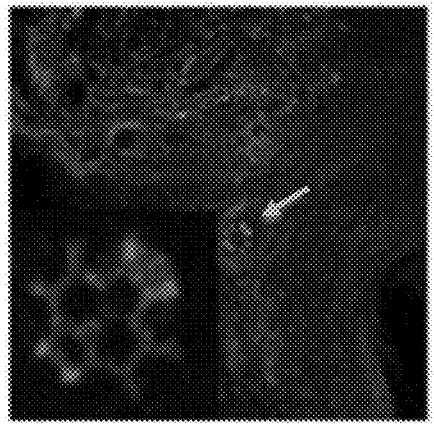
FIG. 12A is a confocal scan image showing a histological section of tissue implanted with a microrobot made using 75 vol % PEGDA and 25 vol % PETA at week 2.
Figure 12C:
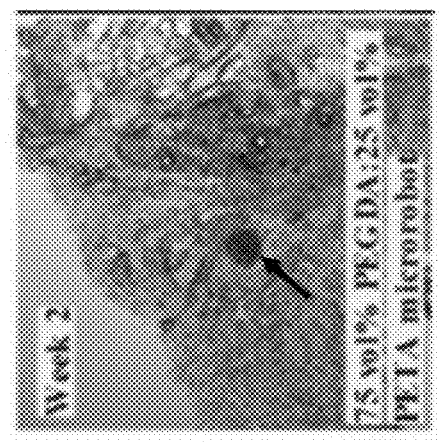
FIG. 12C is a confocal scan image showing a histological section of tissue implanted with a microrobot made with too vol % PETA at week 2.

FIGS. 10A to 10D show the degradation of the microrobot in the NaOH solution and FIGS. 11A and 11B show the degradation of microrobot in the PBS environment. PEGDA-based hydrogel would undergo a bulk mode of degradation. In bulk degradation, no significant change occurs in the physical size of the polymer network until it is almost fully degraded, but the fraction of polymer remaining in the hydrogel decreases over time.

Local tissue environment, enzymatic oxidation, and macrophage activity may impact the hydrogel degradation. In vivo tests of microrobot degradability were performed in the subcutaneous (SC) tissue of nude mice. Degradable 75 vol % PEGDA:25 vol % PETA microrobots and hard-to-degrade 100 vol % PETA microrobots were implanted subcutaneously on the left and right flanks of each mice. All microrobots were manufactured using a prepolymer solution containing 1 mg/mL RB-PEG-SH and rinsed and dried before implantation. Mice were sacrificed at weeks 2 and 4. Skin fragments with a size of about 1×1 cm$^2$ at the implantation regions were excised and fixed with a formaldehyde solution. The fixed skin tissues were then embedded in a cryomatrix frozen medium and cut vertically to a thickness of 50 µm using a cryostat.

Figure 14:
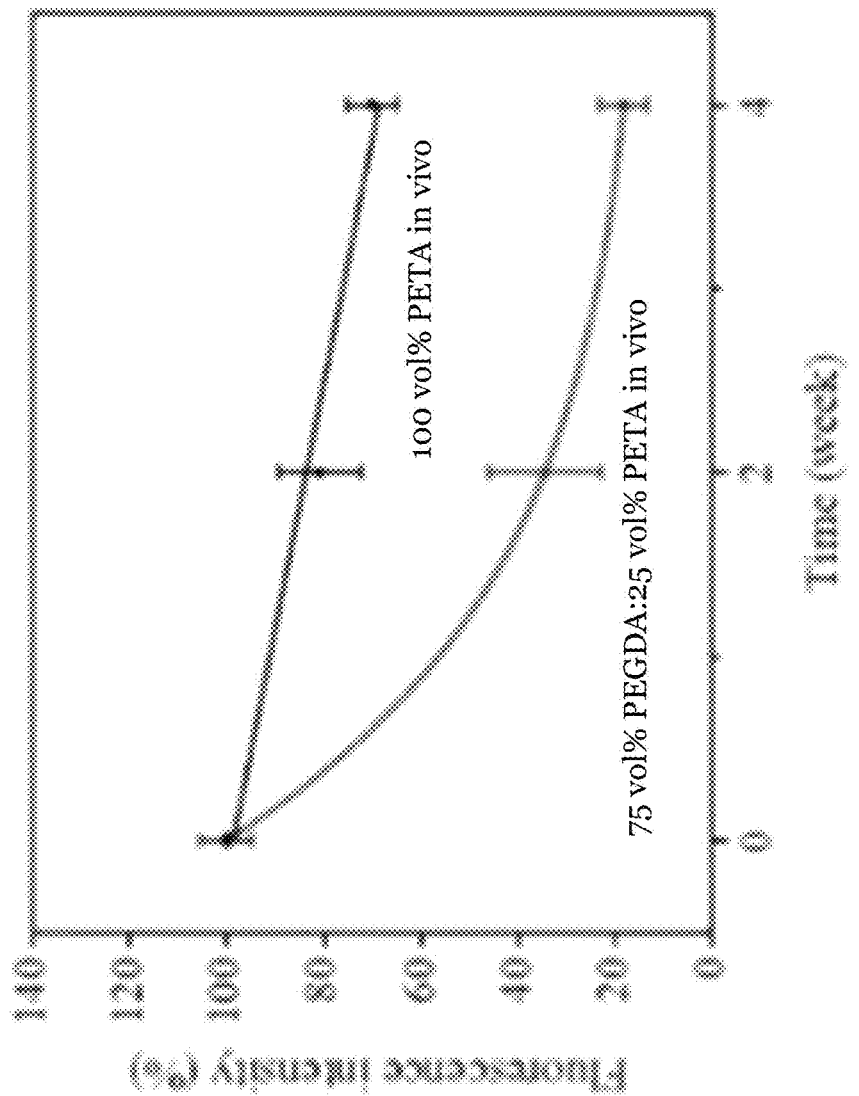
FIG. 14 is a graph showing the fluorescence intensity of the microrobots made with different ratios of PEGDA to PETA in vivo.

FIGS. 12A to 13D show histological sections of tissue implanted with a microrobot. The confocal scan images show that the microrobot was not washed away. The fluorescence signal of rhodamine B was only present in or near the microrobot. There was no leakage of rhodamine B in a large area. The release process of rhodamine B is correlated with the degradation of the microrobot. The fluorescence signal of rhodamine B on the microrobot has been characterized. FIG. 14 shows that the fluorescence intensity of the degradable 75 vol % PEGDA:25 vol % PETA microrobot decreased by about 65% at 2 weeks after implantation, and 82% at 4 weeks after implantation. The hard-to-degrade 100 vol % PETA microrobot decreased by 19% and 30%, respectively. These experimental results confirmed the in vivo degradability of microrobots.

Figures 15A, 15B, 15C:
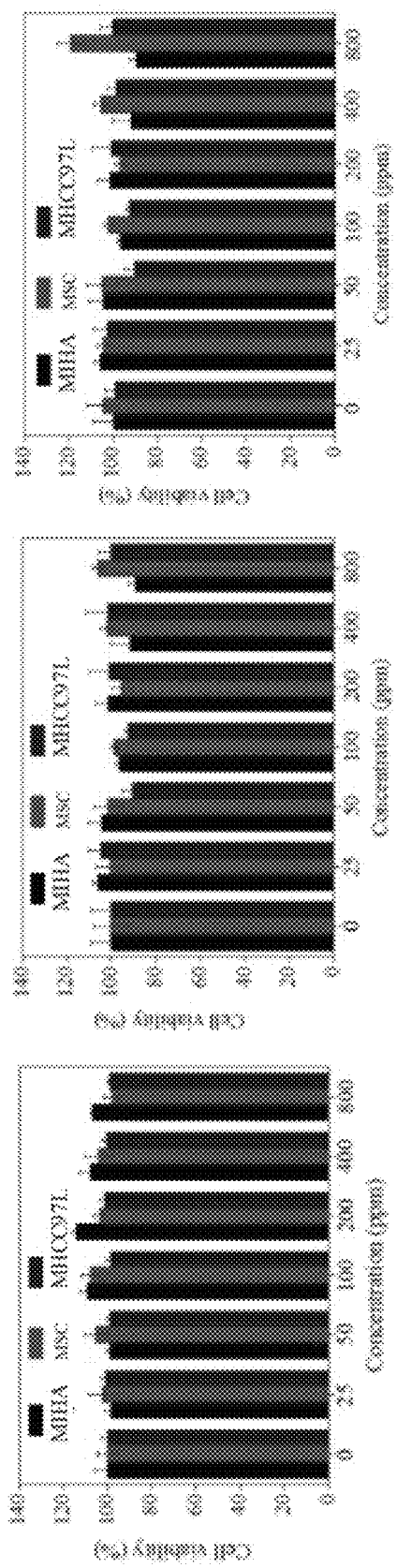
FIG. 15A is a graph showing the cell viability in different cell culture (MIHA, MSC, MNCC97L) with different concentrations of degradation products of the microrobots on Day 1.
FIG. 15B is a graph showing the cell viability in different cell culture (MIHA, MSC, MNCC97L) with different concentrations of degradation products of the microrobots on Day 3.
FIG. 15C is a graph showing the cell viability in different cell culture (MIHA, MSC, MNCC97L) with different concentrations of degradation products of the microrobots on Day 5.

Considering that the degradation products of the microrobot will remain in the body for a certain period of time, a viability test was subsequently performed to examine the biocompatibility of the fully degraded products. MTT assays were performed with cells cultured in the medium supplemented with different concentrations of degradation products on Day 1, 3, and 5. FIGS. 15A to 15C show that even if 800 ppm degradation products were added to the medium (equivalent to degrading 10 k microrobots in 1 uL solution), the cell viability was not substantially impaired. The viability of all cell types was above 80% even under the ultrahigh concentration of degradation products.

In Vivo Imaging of Magnetically-Driven Microrobots

To facilitate in vivo experiments using the microrobots, real-time imaging of microrobots at depths from several millimeters to centimeters can be conducted. In one example, the microrobots were engineered and the PA tomography (PAT) was tailored for in vivo microrobotic imaging. The microrobot was engineered with optically absorbing materials to ensure a high optical absorption coefficient and high contrast to haemoglobin molecules in the visible spectrum. By tuning the optical excitation wavelengths, the contrast of microrobots in blood was optimized and the blood and microrobots were quantified simultaneously. To visualize the tissue environment, the co-registered PA and US images were acquired simultaneously.

In this example, to enhance the PA signal of microrobots and to improve the contrast of microrobots to blood, 1064 nm was chosen for in vivo imaging. The microrobots were coated with a 10 nm-thick layer of gold (photoacoustic imaging contrast agent) to further enhance the absorption while ensuring good biological compatibility. To deliver more therapeutic cells to the diseased site, a cluster (from several to hundreds) of microrobots were used in one treatment. The large number of microrobots increased the PA signal. FIG. 16A illustrates that the PA magnitude is positively correlated with the number of microrobots, both under the 1064 nm laser wavelength. Compared with the uncoated microrobots under the same excitation, the gold-coated microrobots generated a signal five times stronger.

Figure 16B:
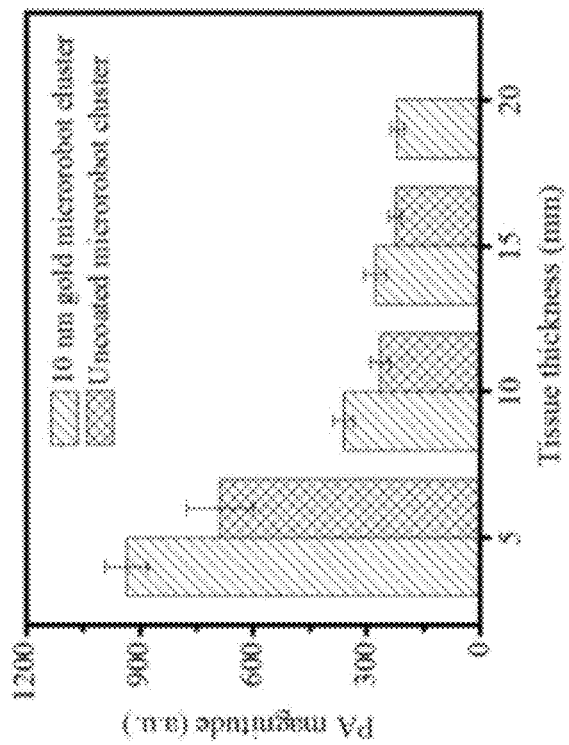
FIG. 16B is a graph showing the comparison of the photoacoustic magnitudes of 10 nm-gold-coated and uncoated microrobots under different tissue thicknesses.
Figure 16A:
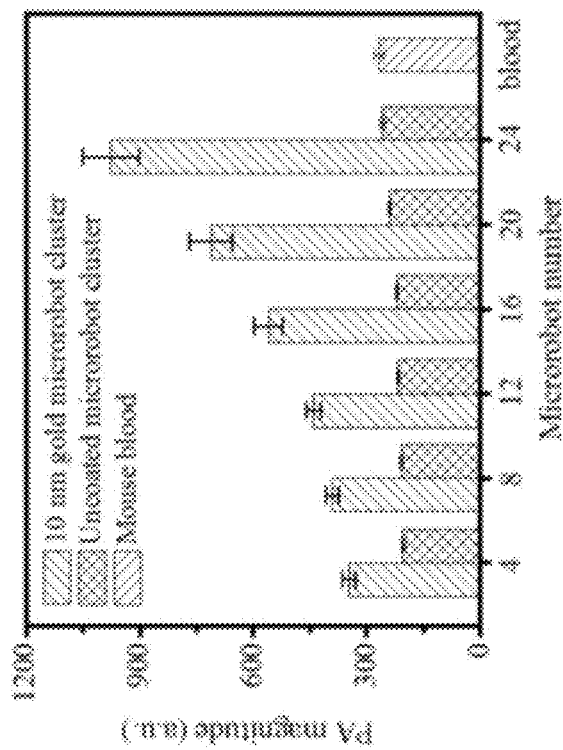
FIG. 16A is a graph showing the comparison of the photoacoustic magnitudes of different numbers of 10 nm-gold-coated and uncoated microrobots.
Figure 17C:
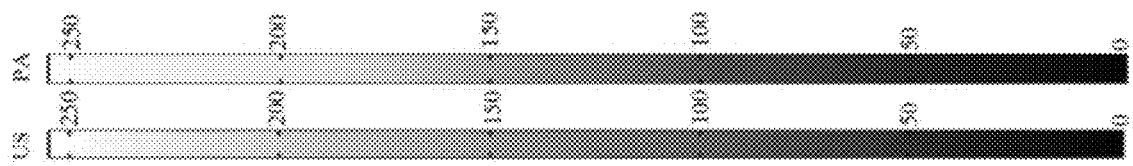
FIG. 17C is a merged ultrasonic-photoacoustic image of the left lateral lobe in FIG. 17A.
Figure 17C:
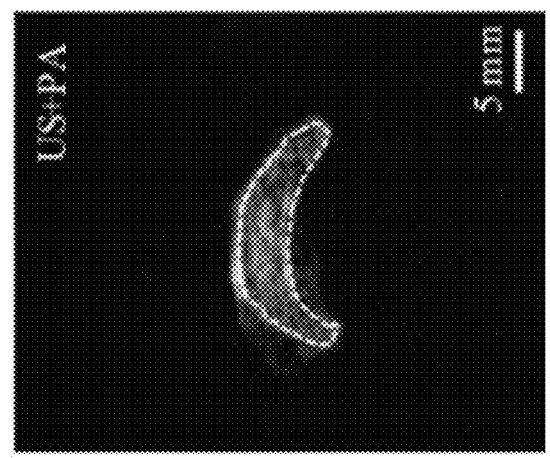
Figure 17B:
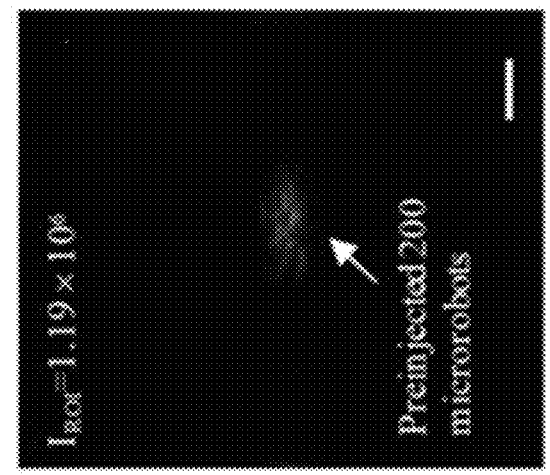
FIG. 17B is a photoacoustic image of the left lateral lobe in FIG. 17A, the arrow indicating the pre-injected 200 microrobots.
Figure 17A:
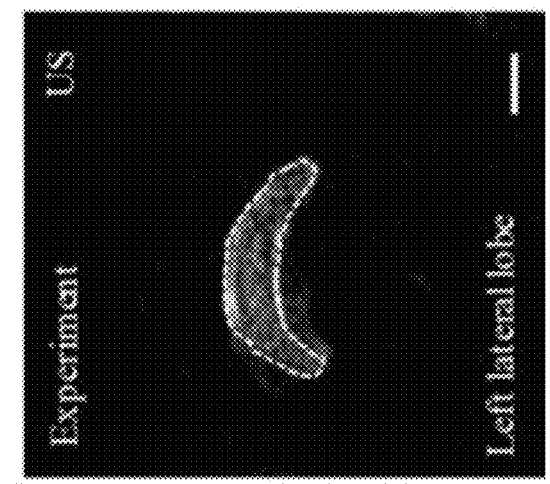
FIG. 17A is an ultrasonic image of the left lateral lobe pre-injected with 200 microrobots.
Figure 18C:
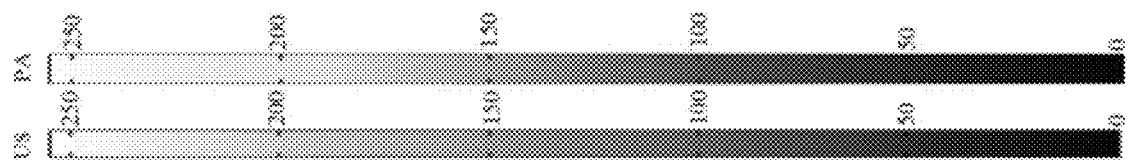
FIG. 18C is a merged ultrasonic-photoacoustic image of the left lateral lobe in FIG. 18A.
Figure 18C:
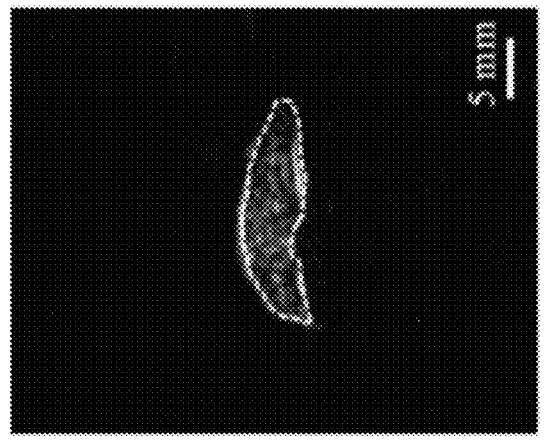
Figure 18B:
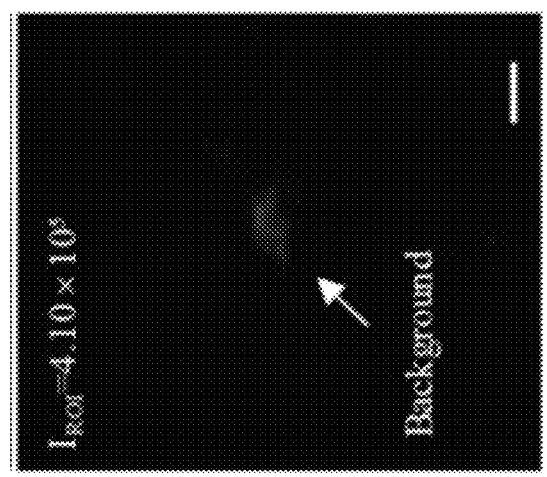
FIG. 18B is a photoacoustic image of the left lateral lobe in FIG. 18A, the arrow indicating the background signals.
Figure 18A:
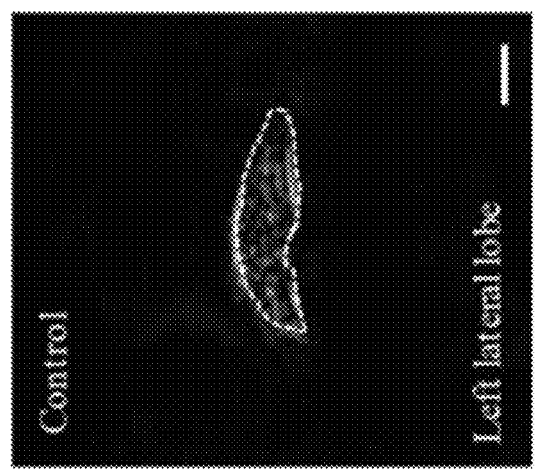
FIG. 18A is an ultrasonic image of the left lateral lobe without microrobots.

To demonstrate microrobotic imaging in deep tissue, two clusters of microrobots were imaged in chicken tissues, as shown in FIG. 16B. One cluster consists of 10 gold-coated microrobots, and the other one consists of 10 uncoated microrobots. Compared with the uncoated microrobot cluster, the coated microrobot exhibited stronger PA signals under various tissue thicknesses. The gold-coated microrobot cluster can be clearly imaged at the depth of 2 cm, whereas the uncoated cluster could hardly be detected at the depth of 2 cm. This experiment shows that the engineered microrobot has good contrast in deep PA imaging.

Imaging of the microrobots was further tested in the mice liver. Two hundred microrobots were injected via the portal vein into the left lateral lobe (LLL), which were then harvested and fixed in paraformaldehyde (PFA), and imaged with US and PAT. FIGS. 17A to 18C show the imaging results. The US images show the morphology of LLL, and the PA images show the absorption contrast of the microrobots against the liver tissue. The merged US and PA images show the position of the microrobot distribution in LLL. The LLL with 200 injected microrobots had a signal amplitude 2.8 times that of the control.

In Vivo Navigation of Magnetically-Driven Microrobots in Mice Model

Figure 19B:
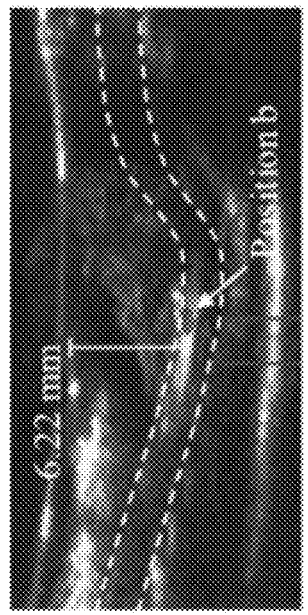
FIG. 19B is a photoacoustic image of the in vivo navigation in FIG. 19A at position b.
Figure 19C:
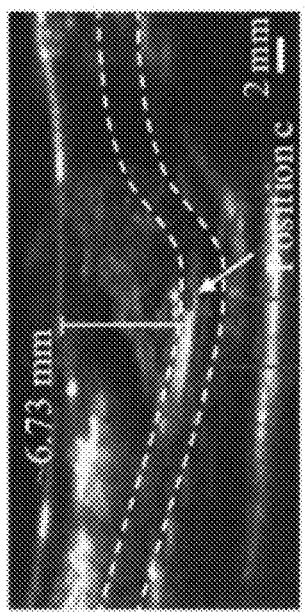
FIG. 19C is a photoacoustic image of the in vivo navigation in FIG. 19A at position c.
Figure 19A:
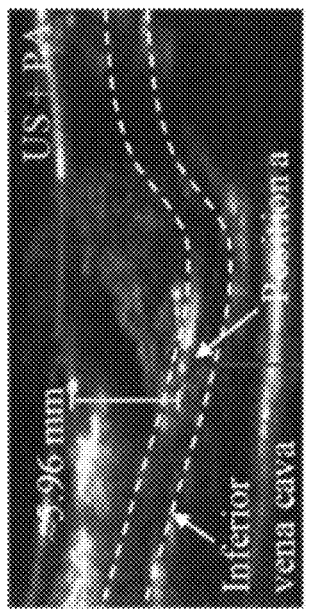
Figure 20:
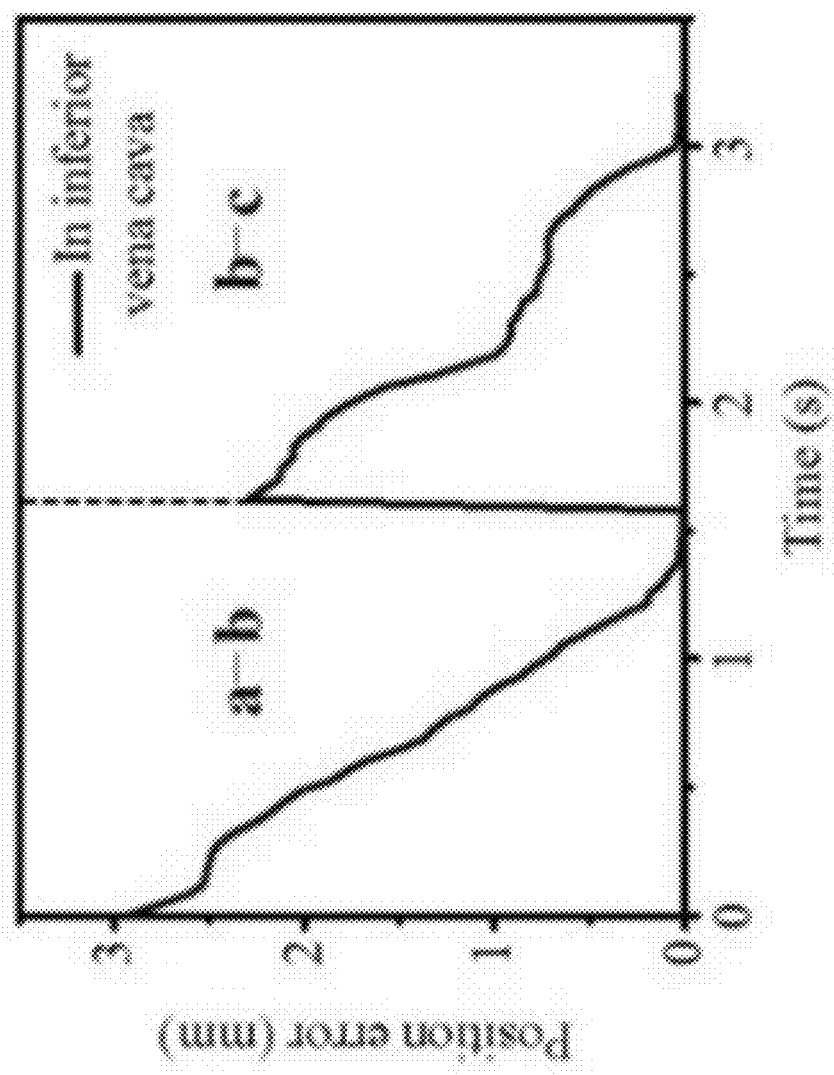
FIG. 20 is a graph showing the position errors of the cell-loaded microrobots at different positions in the inferior vena cava in FIGS. 19A-19C.

In vivo navigation of the cell-loaded microrobots guided by PA imaging was conducted in the inferior vena cava of nude mice at a depth of 6 mm (male, 6 to 8 weeks). The set up was similar to that in FIG. 2. The microrobot cluster consists of five gold-plated microrobots. Using a sharp needle-covered catheter, a cluster of microrobots carrying cells was delivered into the inferior vena cava of nude mice. Guided by real-time PA and US imaging (20 frames per second per imaging mode), the microrobots inside the catheter were activated by using a gradient magnetic field in the vein. A proportional-integral-derivative (PID) controller was used in motion control, and position feedback was obtained by visually processing PA images. During the microrobot navigation, two target positions were set and marked as b and c (FIGS. 19B and 19C, respectively). The cluster of microrobots with cells moved from the starting position a (FIG. 19A) to the target position b, and then from b to the target position c, with a total displacement of 5.1 mm. As shown in FIG. 20, the position error of the microrobot indicates that the microrobot with cells can accurately navigate the vascular environment to transport therapeutic cells.

The above embodiments of the invention have provided a method of making cell-loadable magnetically-drivable, and/or degradable microrobots that facilitate wireless and minimally invasive methods for precise treatment of diseases. In one example, the microrobots can be used for precise cell delivery in the living body of human or other animal, e.g., in the vascular tissues. The microrobots can be navigated and tracked by photoacoustic imaging in vivo for targeted therapy. The microrobots can be degraded after performing the tasks (e.g., delivering cells or drugs), in particular in vivo, with relatively few side effects. The above embodiments of the invention have also provided an imaging method for guiding movements of the microrobots in vivo or in vitro. The photoacoustic imaging can enable real-time navigation and provide images with high resolutions, in particular at millimeters to centimeters of tissues, potentially facilitating surgical and/or therapeutical applications of the microrobots.

It will be appreciated by persons skilled in the art that numerous variations and/or modifications may be made to the illustrated embodiments without departing from the scope of the invention. The described embodiments of the invention should therefore be considered in all respects as illustrative, not restrictive.

The illustrated method for making a microrobot can be used to make microrobots with different structures, shape, form, size, etc. Also, the illustrated microrobot may be manipulated in different environments using methods or systems not illustrated. For example, the method of making microrobots can be different from that illustrated. Different photo-curing techniques, including but not limited to lithography, may be applied to form the microrobots. The method may be used to form one or more microrobots. The photo-curable material composition may include one or more degradable components; one or more structural components; one or more magnetic component; and one or more photo-curing facilitation compositions comprising one or more photoinitiator components and one or more photosensitizer components. The degradable component need not be PEGDA. The structural component need not be PETA. The magnetic component need not be Fe3O4 particles, but can be other ferromagnetic or magnetic materials. Contrast agent may be coated on or applied to at least part of the body. The photo-curable material composition may be photo-cured using techniques other than lithography. Multiple microrobots may be formed (e.g. photo-cured and developed) one after another or substantially simultaneously. Adjacent bodies of the microrobots may be overlapped, e.g. mechanically engaged, with or without direct material connection. For example, the microrobot can be different from that illustrated. The microrobot may have a solid body instead of a porous body. The microrobot may have a non-spherical shape. The burr members on the body of the microrobot may have different orientations, forms, sizes, lengths, etc. In some embodiments, the body of the microrobot may not have any burr members on the body. In some embodiments, the body of the microrobot may include surface recessed portions. The microrobots may be used to carry and deliver cells, drugs, or the like. The illustrated method and system for manipulating the microrobots may be modified for different control applications. The illustrated method and system may be modified to be used other in vivo or in vitro environments. The system for manipulating the microrobots may include additional or alternative means (instead of the sharp needle and the catheter) for delivering the microrobots to or into the environment.

The invention claimed is:

1. A method of making a cluster of magnetically-drivable and in-vivo-degradable microrobots, the method comprising:
    forming a plurality of overlapped bodies of the cluster of magnetically-drivable and in-vivo-degradable microrobots by photo-curing a photo-curable material composition such that
    (i) each of the plurality of overlapped bodies comprises a respective porous body with a three-dimensional structure having burr members, and
    (ii) for each of the plurality of overlapped bodies, one or more of its burr members are mechanically engaged with one or more of the burr members of at least one adjacent body of the plurality of overlapped bodies,
    the photo-curable material composition comprising a degradable component, a structural component, a magnetic component, and a photo-curing facilitation composition comprising a photoinitiator component and a photosensitizer component; and
    coating or applying a photoacoustic imaging contrast agent on at least part of each of the plurality of overlapped bodies.

2. The method of claim 1, wherein the degradable component comprises poly(ethylene glycol) diacrylate (PEGDA) or poly(ethylene glycol) (PEG) derivatives.

3. The method of claim 1, wherein the structural component comprises pentaerythritol triacrylate (PETA).

4. The method of claim 1, wherein the magnetic component comprises Fe3O4 particles.

5. The method of claim 4, wherein the Fe3O4 particles comprise Fe3O4 nanoparticles.

6. The method of claim 1, wherein the photo-curing is performed selectively using lithography.

7. The method of claim 6, wherein the photo-curing is performed selectively using 3D laser lithography or multiphoton lithography.

8. The method of claim 1, wherein the photoacoustic imaging contrast agent comprises gold.

9. The method of claim 1, further comprising forming the photo-curable material composition by
    mixing the degradable component and the structural component based on a first ratio to form a first mixture, and
    mixing the first mixture with the magnetic component based on a second ratio to form a second mixture.

10. The method of claim 9, further comprising determining a composition of the photo-curable material composition prior to the forming of the photo-curable material composition.

11. The method of claim 10, wherein determining the composition of the photo-curable material composition comprises determining the first and second ratios.

12. The method of claim 1, further comprising mixing the photo-curable material composition prior to the photo-curing.

13. The method of claim 1, further comprising developing each of the plurality of overlapped formed bodies after the photo-curing.

14. The method of claim 1, wherein the degradable component comprises poly(ethylene glycol) diacrylate (PEGDA) and the structural component comprises pentaerythritol triacrylate (PETA); and wherein a ratio of vol % of PEGDA to vol % of PETA is about 3:1.

15. The method of claim 1, wherein the mechanical engagement is without direct material connection.

16. The method of claim 1, further comprising attaching or loading cells to one or more of the plurality of bodies and/or the coating such that at least some of the cells are loaded or attached between different ones of the burr members of adjacent ones of the microrobots.

17. The method of claim 1,
wherein the degradable component comprises poly(ethylene glycol) diacrylate (PEGDA) or poly(ethylene glycol) (PEG) derivatives,
wherein the structural component comprises pentaerythritol triacrylate (PETA), and
wherein the magnetic component comprises $Fe_3O_4$ particles.

18. A cluster of magnetically-drivable and in-vivo-degradable microrobots, comprising:
a plurality of overlapped bodies made by photo-curing of a photo-curable material composition, each of the plurality of overlapped bodies comprising a respective porous body with a three-dimensional structure having burr members, and for each of the plurality of overlapped bodies, one or more of its burr members are mechanically engaged with one or more of the burr members of at least one adjacent body of the plurality of overlapped bodies,
wherein the photo-curable material composition includes:
a degradable component, a structural component, a magnetic component, and a photo-curing facilitation composition comprising a photoinitiator component and a photosensitizer component; and
a photoacoustic imaging contrast agent coated or arranged on at least part of each of the plurality of overlapped bodies.

* * * * *